US012576098B2

(12) United States Patent
Wei et al.

(10) Patent No.: US 12,576,098 B2
(45) Date of Patent: Mar. 17, 2026

(54) **SAPONIN CONTAINING EXTRACTS PREPARED FROM *HESPERALOE* USEFUL IN THE TREATMENT OF NON-HUMAN ANIMALS**

(71) Applicant: KIMBERLY-CLARK WORLDWIDE, INC., Neenah, WI (US)

(72) Inventors: Ning Wei, Roswell, GA (US); Thomas G. Shannon, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 482 days.

(21) Appl. No.: 18/011,326

(22) PCT Filed: Jun. 21, 2021

(86) PCT No.: PCT/US2021/038272
§ 371 (c)(1),
(2) Date: Dec. 19, 2022

(87) PCT Pub. No.: WO2021/258055
PCT Pub. Date: Dec. 23, 2021

(65) Prior Publication Data
US 2023/0302110 A1 Sep. 28, 2023

Related U.S. Application Data

(60) Provisional application No. 63/041,224, filed on Jun. 19, 2020.

(51) Int. Cl.
| | |
|---|---|
| *A61K 31/7048* | (2006.01) |
| *A23K 10/30* | (2016.01) |
| *A23K 20/121* | (2016.01) |
| *A23K 20/163* | (2016.01) |
| *A23K 50/75* | (2016.01) |
| *A61K 31/704* | (2006.01) |
| *A61K 36/896* | (2006.01) |
| *A61K 36/8965* | (2006.01) |
| *A61K 39/00* | (2006.01) |
| *A61K 39/012* | (2006.01) |
| *A61K 39/39* | (2006.01) |
| *A61P 1/14* | (2006.01) |
| *A61P 33/02* | (2006.01) |

(52) U.S. Cl.
CPC .......... *A61K 31/7048* (2013.01); *A23K 10/30* (2016.05); *A23K 20/121* (2016.05); *A23K 20/163* (2016.05); *A23K 50/75* (2016.05); *A61K 31/704* (2013.01); *A61K 36/896* (2013.01); *A61K 36/8965* (2013.01); *A61K 39/012* (2013.01); *A61K 39/39* (2013.01); *A61P 1/14* (2018.01); *A61P 33/02* (2018.01); *A61K 2039/55577* (2013.01)

(58) Field of Classification Search
CPC ................................ A23K 10/30; A23K 50/75
See application file for complete search history.

(56) References Cited

U.S. PATENT DOCUMENTS

| | | | |
|---|---|---|---|
| 5,597,807 | A | 1/1997 | Estrada et al. |
| 6,891,079 | B2 | 5/2005 | Koenig et al. |
| 7,154,018 | B2 | 12/2006 | Koenig et al. |
| 7,478,610 | B2 | 1/2009 | Tsengas et al. |
| 2011/0236438 | A1 | 9/2011 | Aharon et al. |
| 2015/0190452 | A1 | 7/2015 | Hwang et al. |
| 2017/0072002 | A1 | 3/2017 | Bafundo et al. |

(Continued)

FOREIGN PATENT DOCUMENTS

| | | |
|---|---|---|
| CN | 1286979 A | 3/2001 |
| CN | 1145490 C | 4/2004 |

(Continued)

OTHER PUBLICATIONS

Alfaro D. M. et al., "Use of Yucca schidigera Extract in Broiler Diets and Its Effects on Performance Results Obtained with Different Coccidiosis Control Methods", Dec. 31, 2007, https://www.researchgate.net/publication/255655374_Use_of_Yucca_schidigera_Extract_in_Broiler_Diets_and_Its_Effects_on_Performance_Results_Obtained_with_Different_Coccidiosis_Control_Methods.

(Continued)

*Primary Examiner* — Brian Gangle
*Assistant Examiner* — Lakia J Jackson-Tongue
(74) *Attorney, Agent, or Firm* — Kilpatrick Townsend & Stockton LLP

(57) ABSTRACT

Disclosed are novel pharmaceutical, animal feed compositions and methods of treating non-human animals comprising at least one component selected from the extract(s), fraction(s), active compound(s) and phytochemical(s), or mixtures thereof, derived from non-woody plants of the genus *Hesperaloe*. Animal feed compositions may comprise a basal animal feed and water soluble solids extracted from *Hesperaloe* and comprising at least one saponin. The water soluble solids may comprise from about 5 to about 30 wt % saponin. The compositions of the present invention can be used for the treatment of non-human animals, such as poultry and more particularly for preventing and treating coccidiosis. An embodiment provides an immunological composition useful for inducing the production of antibodies to an antigen in a non-human animal comprising an antigen, preferably a coccidia, and a saponin composition extracted from *Hesperaloe*. The saponins extracted from *Hesperaloe* biomass may comprise 25(27)-dehydrofucreastatin, 5(6),25 (27)-disdehydroyuccaloiside C, 5(6)-disdehydroyuccaloiside C, furcreastatin and yuccaloiside C.

21 Claims, 4 Drawing Sheets

(56) References Cited

U.S. PATENT DOCUMENTS

| | | | |
|---|---|---|---|
| 2017/0128401 A1 | 5/2017 | Dooney et al. | |
| 2017/0290768 A1 | 10/2017 | Barzilay et al. | |
| 2018/0333450 A1 | 11/2018 | McNeff et al. | |
| 2019/0060341 A1 | 2/2019 | Leal Díaz et al. | |
| 2023/0263815 A1 | 8/2023 | Wei et al. | |
| 2023/0302079 A1* | 9/2023 | Wei | A61K 31/7048 |

FOREIGN PATENT DOCUMENTS

| | | | |
|---|---|---|---|
| CN | 101341930 B | 1/2011 | |
| CN | 102076358 A | 5/2011 | |
| CN | 101696138 B | 10/2012 | |
| CN | 103907762 A | 7/2014 | |
| CN | 104256097 A | 1/2015 | |
| CN | 104719641 A | 6/2015 | |
| CN | 105594662 A | 5/2016 | |
| CN | 106173232 A | 12/2016 | |
| CN | 106417915 A | 2/2017 | |
| CN | 106492092 A | 3/2017 | |
| CN | 106659787 A | 5/2017 | |
| CN | 106889319 A | 6/2017 | |
| CN | 108497173 A | 9/2018 | |
| CN | 108651737 A | 10/2018 | |
| CN | 109198254 A | 1/2019 | |
| CN | 110464791 A | 11/2019 | |
| CN | 111268782 A | 6/2020 | |
| EP | 1082909 A1 | 3/2001 | |
| EP | 0773786 B1 | 6/2001 | |
| EP | 1304041 B1 | 4/2005 | |
| EP | 3056214 B1 * | 3/2019 | |
| JP | 2000281698 A | 10/2000 | |
| JP | 2006061092 A | 3/2006 | |
| KR | 20110026669 A | 3/2011 | |
| WO | 2015179840 A1 | 11/2015 | |
| WO | 2018100386 A1 | 6/2018 | |
| WO | 2021258055 A1 | 12/2021 | |
| WO | 2021258056 A1 | 12/2021 | |
| WO | 2021258059 A1 | 12/2021 | |

OTHER PUBLICATIONS

CN Application No. 202180061169.6 , "Office Action", Jun. 29, 2024, 14 pages.

EP Application No. 21826299.6 , "Extended European Search Report", Jul. 9, 2024, 9 pages.

EP Application No. 21826613.8 , "Extended European Search Report", Jul. 29, 2024, 7 pages.

Brazilian Application No. BR112022025449-0 "Office Action", Mar. 6, 2025, 6 pages.

Chinese Application No. CN202180043971.2, "Office Action", Dec. 31, 2024, 20 pages.

Ayoub et al., "Effects of Liquid Yucca Supplementation on Nitrogen Excretion, Intestinal Bacteria, Biochemical and Performance Parameters in Broilers.", Animals, Dec. 9, 2009, https://www.ncbi.nlm.nih.gov/pmc/articles/PMC6940917/.

Dimitriou et al., "The effects of Yucca shidigera extract on the reduction of ammonia concentration in Lake Koumoundourou", Apr. 2013, InEGU General Assembly Confernce Abstracts, https://ui.adsabs.harvard.edu/abs/2013EGUGA..15.3095D/abstract.

Eugenio et al., "Evaluation of Hesperaloe Funifera Pulps Obtained by a Low Energy Consumption Process as a Reinforcement Material in Recycled Pulps", Mar. 3, 2012, Forest Systems, http://revistas.inia.es/index.php/fs/article/view/3691/1737.

Marker et al., "Steroidal Sapogenins. No. 171. Biogenesis of the Steroidal Sapogenins in Agaves, Manfreda and Hesperaloe", Oct. 1947, J. Am. Chem. Soc., http://pubs.acs.org/doi/abs/10.1021/ja01202a047.

Marker et al., Sterols. CLVII. Sapogenins. LXIX. Isolation and Structures of Thirteen New Steroidal Sapogenins, J. Am. Chem. Soc. Jun. 1, 1943, https://sci-hub.ru/10.1021/ja01246a051.

Martinez-Cordova et al., "Yucca extract reduces ammonia concentrations in Mexico shrimp trial", Jun. 1, 2003, https://www.aquaculturealliance.org/advocate/yucca-extract-reduces-ammonia-concentrations-in-mexico-shrimp-trial/.

Martin-Sampedro et al., "Effect of Steam Explosion and Enzymatic Pre-Treatments on Pulping and Bleaching of Hesperaloe Funifera", Feb. 11, 2012, Bioresource Technology, http://www.sciencedirect.com/science/article/pii/S0960852412002520.

Sanchez et al., "Hesperaloe Funifera as a Raw Material for Integral Utilization of its Components", 2011, BioResources, http://ojs.cnr.ncsu.edu/index.php/BioRes/article/view/BioRes_06_1_0003_Sanchez_FSTLR_Hesperaloe_Material_Integral_Utilization/784.

Sanchez et al., "Use of Hesperaloe Funifera for the Production of Paper and Extraction of Lignin for Synthesis and Fuel Gases", May 14, 2010, Biomass and Bioenergy, http://www.sciencedirect.com/science/article/pii/S0961953410001467.

Santacruz-Reyes et al., "The potential of Yucca schidigera extract to reduce the ammonia pollution from shrimp farming.", Jun. 1, 2012, Bioresource Technology, https://pubmed.ncbi.nlm.nih.gov/22440573/.

Simmons-Boyce et al., "Steroidal Saponins and Sapogenins from the Agavaceae Family", Natural Product Communications, Jan. 1, 2007, https://journals.sagepub.com/doi/epdf/10.1177/1934578X0700200120.

Sinurat et al., "Utilization of plant bioactives as feed additives for poultry: The effect of Aloe vera gel and its extract on performance of broilers", Nov. 9, 2003, Indonesian Journal of Animal and Veterinary Sciences, http://medpub.litbang.pertanian.go.id/index.php/jitv/article/view/384.

Chinese Application No. 202180061169.6, Office Action mailed on Dec. 27, 2023, 17 pages.

International Application No. PCT/US2021/038274, International Preliminary Report on Patentability mailed on Dec. 29, 2022, 9 pages.

International Application No. PCT/US2021/038274, International Search Report and Written Opinion mailed on Oct. 12, 2021, 15 pages.

U.S. Appl. No. 18/011,341, "Restriction Requirement", Jun. 20, 2025, 9 pages.

U.S. Appl. No. 18/011,335, "Non-Final Office Action", Aug. 15, 2025, 40 pages.

U.S. Appl. No. 18/011,341, "Office Action", Sep. 24, 2025, 29 pages.

Brazilian Patent Application No. BR112022025447-4, "Office Action", May 20, 2025, 9 pages, search and written opinion.

Chinese Application No. 202180043971.2, "Office Action", Aug. 14, 2025, 22 pages.

Chinese Patent Application No. 201280061347.5, "First Office Action", Jun. 19, 2025, 16 pages.

European Application No. 21825033.0, "Extended European Search Report", Jul. 29, 2024, 12 pages.

Glade , "Effects of Yucca Shidigera Extract on Feed Utilization by Equine Weanlings", Journal of Equine Veterinary Science, vol. 12, No. 2, XP022311759, Mar. 1, 1992, pp. 93-98.

Japanese Patent Application No. 2022-576129, "Office Action", Apr. 22, 2025, 8 pages.

Japanese Patent Application No. 2022-577719, "Office Action", Jul. 15, 2025, 23 pages.

PCT International Preliminary Report on Patentability of the International Searching Authority, PCT/US2021/038278, Dec. 13, 2022, 8 pages.

PCT International Preliminary Report on Patentability of the International Searching Authority, PCT/US2021/038272, mailed Dec. 13, 2022, 8 pages.

PCT International Search Report and Written Opinion of the International Searching Authority, PCT/US2021/038278, Oct. 12, 2021, 12 pages.

PCT International Search Report and Written Opinion of the International Searching Authority, PCT/US2021/038272, mailed Oct. 12, 2021, 15 pages.

Vietnamese Patent Application No. 1-2023-00151, "Office Action", May 30, 2025, 6 pages.

(56) References Cited

OTHER PUBLICATIONS

Vietnamese Patent Application No. 1-2023-00216, "Office Action", Feb. 28, 2025, 4 pages.

Wooton, E.O., Certain desert plants as emergency stock feed (No. 728), US Department of Agriculture. (Year: 1918).

Indonesian Patent Application No. P00202300350, "Office Action", May 26, 2025, 3 pages.

Vietnamese Patent Application No. 1-2023-00181, "Office Action", May 29, 2025, 4 pages.

Japanese Patent Application No. 2022-576124, "Office Action", Jul. 15, 2025, 21 pages.

Indonesian Patent Application No. P0020230038, "Office Action", Oct. 13, 2025, 6 pages.

Japanese Patent Application No. 2022-576129, "Notice of Allowance", Oct. 15, 2025, 2 pages.

Vietnamese Patent Application No. 1-2023-00181, "Office Action", digitally signed Oct. 15, 2025, 8 pages.

Chinese Patent Application No. 202180043971.2, "Office Action", Jan. 7, 2026, 18 pages. pages are not legible.

European Patent Application No. 21826299.6, "Office Action", Jan. 5, 2026, 6 pages.

Japanese Patent Application No. 2022-576124, "Office Action", Jan. 20, 2026, 6 pages.

Japanese Patent Application No. 2022-577719, "Office Action", Jan. 20, 2026, 8 pages.

Philippines Patent Application No. 1-2022-553343, "Office Action", Jan. 8, 2026, 5 pages.

Philippines Patent Application No. 1-2022-553344, "Office Action", Jan. 8, 2026, 5 pages.

European Patent Application No. 21825033.0, "Office Action", Jan. 5, 2026, 6 pages.

Philippines Patent Application No. 1-2022-553345 , "Office Action", Jan. 22, 2026, 5 pages.

Thai Patent Application No. 2201008234, "Office Action", Oct. 29, 2025, 8 pages.

Vietnamese Patent Application No. 1-2023-00216, "Office Action", signed Nov. 11, 2025, 4 pages.

European Patent Application No. 21826613.8, "Office Action", Dec. 9, 2025, 7 pages.

Calle et al., "Steroidal Saponins from Furcraea Hexapetala Leaves and their Phytotoxic Activity", Journal of Natural Products, vol. 79, No. 11, Nov. 23, 2016, pp. 2903-2911.

Itabashi et al., "A New Bioactive Steroidal Saponin, Furcreastatin, from The Plant Furcraea Foetida", Carbohydrate Research Pergamon, GB, vol. 323, No. 1-4, XP004186500, Jan. 12, 1999, pp. 57-62.

* cited by examiner

SAPONIN CONTAINING EXTRACTS PREPARED FROM *HESPERALOE* USEFUL IN THE TREATMENT OF NON-HUMAN ANIMALS

CROSS-REFERENCE TO RELATED APPLICATIONS

This application is a U.S. national phase under 35 U.S.C. § 371 of International Patent Application No. PCT/US2021/038272 filed Jun. 21, 2021, which claims the benefit of and priority to U.S. Provisional Application No. 63/041,224 filed Jun. 19, 2020, each of which are incorporated herein by reference in their entirety for all intents and purposes.

BACKGROUND

Plants produce a vast and diverse assortment of organic compounds, the great majority of which do not appear to participate directly in their growth and development. These substances, traditionally referred to as secondary metabolites or plant natural products, often are distributed among limited taxonomic groups within the plant kingdom. The functions of secondary metabolites remain largely unknown, although a number of compounds have been associated with attributes useful to the plants e.g. protection against herbivores and protection against microbial infection, as attractants for pollinators and seed-dispersing animals, and as compounds that influence competition among plant species (allelochemicals). There is a growing interest in plant natural products, since these products often have a wide range of applications in different kinds of industries, including pharmaceutical industries, cosmetic industries, food industries, detergent industries, and the like.

A particular group of plant secondary metabolites of interest are saponins. Saponins are glycosylated compounds classified as either triterpenoids, steroids, or steroidal glycoalkaloids. Saponins consist of one or two sugar moieties which are coupled to the aglycon (mono- and bisdesmosides, respectively). Saponins can be hydrolyzed to sapogenins and sugar moieties by acid hydrolysis or enzymatic methods. Saponins are generally water soluble high molecular weight compounds with molecular weights ranging from 600 to more than 2,000 daltons.

The asymmetric distribution of their hydrophobic (aglycone) and hydrophilic (sugar) moieties confers an amphipathic character to these compounds which are largely responsible for their detergent-like properties. The ability of lowering surface tension make saponins potentially well suited for use in the cosmetic and in the detergent industries. Saponins also have the ability of forming insoluble complexes with cholesterol, which makes some of them suitable for use in the pharmaceutical industry as cholesterol lowering agents. Other saponins are associated with formation of immunostimulating complexes that are useful in vaccine strategies.

Currently, a major limitation to the broad exploitation of saponins is the fact that commercially available saponins are relatively expensive. The expenses is due in large part to the limited number of plant extracts having significant amounts of saponins. Currently, commercially available plant extracts containing saponins include *Saponaria officinalis, Quillaia* bark and stem, *Castanea sativa* seeds, and extracts of various *Yucca* species.

Plant extracts containing saponins are thus of general interest within a wide range of different industries. There is therefore a growing need in the art for alternative sources of saponin extracts and these plant sources should preferably be cheap, easy to obtain, and preferably the saponin content should be relatively high.

SUMMARY

The present inventor have now discovered that water soluble solids extracted from non-woody plants of the genus *Hesperaloe* comprise one or more saponins. The inventors have further discovered that the *Hesperaloe* extracts are useful in improving the immune function of non-human animals. Accordingly, in one embodiment, the present invention provides novel pharmaceutical, dietary supplements and food ingredient compositions that are safe for non-human animal consumption, have beneficial health effects and can enhance the growth of the animals.

In other embodiments, the present invention provides novel pharmaceutical, dietary supplements and food ingredient compositions comprising at least one component selected from the extract(s), fraction(s), active compound(s) and phytochemical(s), or mixtures thereof, derived from non-woody plants of the genus *Hesperaloe* including, for example, *Hesperaloe funifera, Hesperaloe nocturna, Hesperaloe parviflora,* and *Hesperaloe chiangii,* optionally containing one or more of pharmaceutically and dietetically acceptable phytochemical actives, diluents, vehicles, carriers, and actives or mixtures thereof.

In a particularly preferred embodiment, the present invention provides an animal feed additive comprising water soluble solids derived from non-woody plants of the genus *Hesperaloe.* Preferably the water soluble solids comprise at least about 5 wt % saponin, more preferably at least about 10 wt % saponin and still more preferably at least about 15 wt % saponin, such as from about 5 to about 30 wt % saponin, such as from about 15 to about 25 wt % saponin, wherein the weight percentages are based upon the total bone dry weight of the water soluble solids. In a particularly preferred embodiment, the present invention provides an animal feed composition comprising an animal feed and a mixture of steroidal saponins derived from non-woody plants of the genus *Hesperaloe.*

In certain embodiments the mixture of steroidal saponins may have at least one of the following aglycones or genins: kammogenin, manogenin, gentrogenin, hecogenin, tigogenin, sarsapogenin, chlorogenin and gitogenin or their corresponding isomer or oxidized or reduced forms with at least one of the following glycosidic moieties (in the form of acid or salt): glucose, xylose, rhamnose, arabinose, or galactose. In other embodiments the steroidal saponins may comprise agamenoside, agaveside, agavoside, magueyside, agavasaponi, cantalasaponin, sisalsaponin, gabrittonoside, dongnoside or amolonin, or other steroidal saponins. In particularly preferred embodiments the mixture of steroidal saponins comprise 25(27)-dehydrofucreastatin (FIG. 2A), 5(6),25(27)-disdehydroyuccaloiside C (FIG. 2B), 5(6)-disdehydroyuccaloiside (FIG. 2C), furcreastatin and yuccaloiside C.

In other embodiments the present invention provides use of saponin extracts derived from non-woody plants of the genus *Hesperaloe* for the prevention, treatment, and control of one or more conditions in non-human animals, especially birds and more particularly poultry. For example, saponin containing compositions derived from *Hesperaloe* biomass may be administered to non-human animals to reduce environmental ammonia and odor, to provide a hypocholesterolemic effect, reduce inflammation, provide an anti-protozoal effect, control parasitic nematodes, promote weight gain and improve feed conversion efficiency. In a particularly preferred embodiment, the saponin compositions of the present invention may be administered orally to poultry for the prevention and treatment of coccidiosis.

In another embodiment the present invention provides an animal feed composition comprising an animal feed; and a water soluble composition extracted from a non-woody plant of the genus *Hesperaloe* and comprising at least one saponin. In a particularly preferred embodiment total amount of saponin, based upon the total mass of feed, ranges from about 1.0 to about 30.0 grams per 100 kilograms of feed.

In still other embodiments the present invention is directed to preventing an infectious disease in poultry by orally administering a saponin composition derived from non-woody plants of the genus *Hesperaloe*. A particular aspect of the present invention is directed to a method for enhancing the immune response and natural resistance of poultry against coccidia by supplementing a diet of the poultry with a saponin composition of the present invention. Preferably, after hatching, the diet of the poultry is supplemented with the saponin composition of the present invention in an amount of at least about 50 grams of water soluble solids per metric ton of feed, more preferably at least about 100 g/MT, such as from about 50 to about 1,600 g/MT, such as from about 100 to about 1,000 g/MT. The feed composition may be continuously fed to the poultry for at least 7 days, such as at least about 14 days, such as at least about 21 days.

In yet other embodiments the present invention provides an immunological composition useful for inducing the production of antibodies to an antigen in a non-human animal comprising an immunogenically effective amount of an antigen and a saponin composition extracted from a non-woody plants of the genus *Hesperaloe*, wherein the amount of saponin in the extract is present in an amount sufficient to enhance the immune response of the non-human animal to the antigen. In particularly preferred embodiments saponin containing extracts of the present invention are administered with an *Eimeria* vaccine to poultry in need thereof to increase the immune response, lower lesion scores and reduced oocyst shedding resulting from coccidiosis.

In still other embodiments the present invention provides a method of enhancing an immune response to an antigen in a non-human animal comprising administration of a saponin containing extract prepared by extracting biomass derived from non-woody plants of the genus *Hesperaloe* to a non-human animal in an amount sufficient to enhance the immune response of the non-human animal to the antigen.

In another embodiment the invention provides a saponin extract prepared by extracting biomass derived from non-woody plants of the genus *Hesperaloe*. The extraction process may comprise milling the biomass using a tandem mill or a screw press. In other instances, the extraction process may comprise non-mechanical means such as diffusion. For example, in certain instances, the invention provides water soluble solids comprising a mixture of steroidal saponins extracted from *Hesperaloe* biomass by cutting the biomass, milling the biomass, extracting the biomass with a solvent, imbibing the biomass with juice, separating water insoluble solids from the juice and optionally concentrating the juice.

In yet other embodiments the present invention provides a method of processing biomass derived from a non-woody plants of the genus *Hesperaloe* through a series of mills, such as two, three, four, five, six or seven mills, optionally with imbibition and/or depithing, to remove saponins from the biomass in the form of a crude juice. The water-soluble fraction of the crude juice may comprise from about 10 to about 30 wt % saponin. In certain instances, the composition may be concentrated and treated to remove impurities to yield a mixture of saponins as its principle component.

In still other embodiments, the invention provides a process for preparing a substantially pure saponin composition comprising the steps of mixing a juice extracted from a non-woody plants of the genus *Hesperaloe* with a salt and a solvent to form a first solution, adjusting the pH of the first solution to about 6.0 to about 7.0, adding at least one phosphate to the first solution to form an ion-polysaccharides precipitated and removing the precipitated, such as by filtration, to yield a substantially pure saponin composition. In certain instances, the first solution may be heated to facilitate precipitation of the ion-polysaccharides complexes.

DESCRIPTION OF THE DRAWINGS

FIGS. 1A and 1B illustrate a triterpenoid saponin and a steroidal saponin, respectively.

DEFINITIONS

Figure 2A:
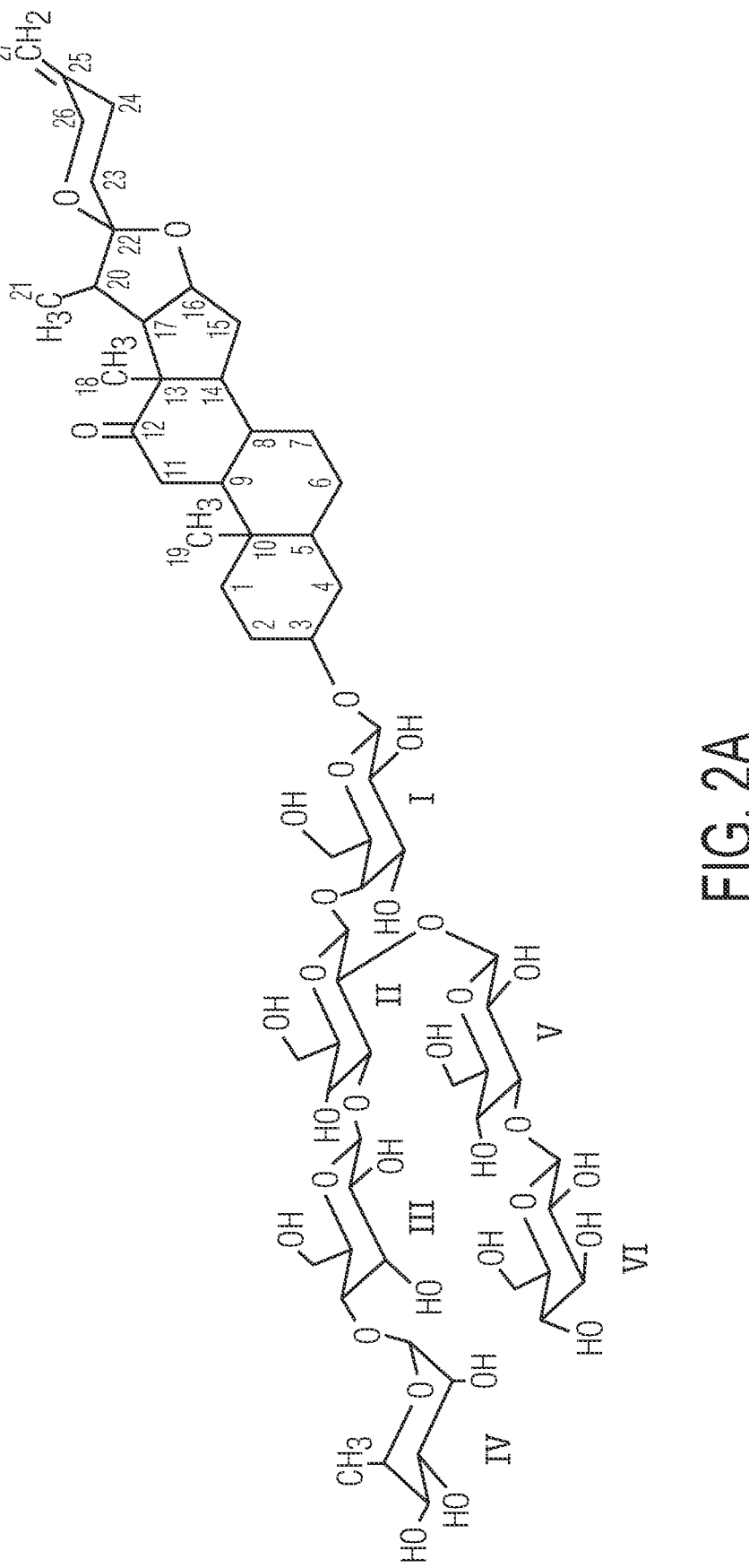
FIGS. 2A-C illustrate various novel saponins extracted from non-woody plants of the genus *Hesperaloe* according to the present invention including, 25(27)-dehydrofucreastatin (FIG. 2A), 5(6),25(27)-disdehydroyuccaloiside C (FIG. 2B), and 5(6)-disdehydroyuccaloiside C (FIG. 2C).

As used herein the term "biomass" generally refers to whole plants and plant organs (i.e., leaves, stems, flowers, roots, etc.) of the genus *Hesperaloe* including, for example, *Hesperaloe funifera, Hesperaloe nocturna, Hesperaloe parviflora*, and *Hesperaloe chiangii*.

As used herein the term "bagasse" generally refers to biomass that has been cut to size and then subjected to high pressure so that the resulting material has less liquid than the biomass from which it is derived. High pressure can be achieved by using compression pressure, such as that provided by machines such one or more opposed counter-rotating rolls, a mechanical press, a screw press as well as by direct hydraulic pressure and other processes to apply pressure to the biomass and remove intercellular and intracellular liquid.

As used herein the term "milling" generally refers to the application of sufficient pressure to force the intercellular and intracellular liquid from the biomass.

As used herein, the term "saccharide" is used interchangeably with the terms "polysaccharide," "oligosaccharide" and "sugar" the definitions of which are well known to those skilled in the art of carbohydrate chemistry. It should be noted that the saccharides can be in the form of mono-, oligo- and/or polysaccharides. Preferably saccharides are water soluble and do not include cellulose, hemicellulose or mono-, oligo- and/or polysaccharides bound to other compounds, such as glycosides (arabinose, glucose, galactose, xylose, and glucuronic acid) bound to a triterpenoid to form a saponin.

Figures 1A, 1B:
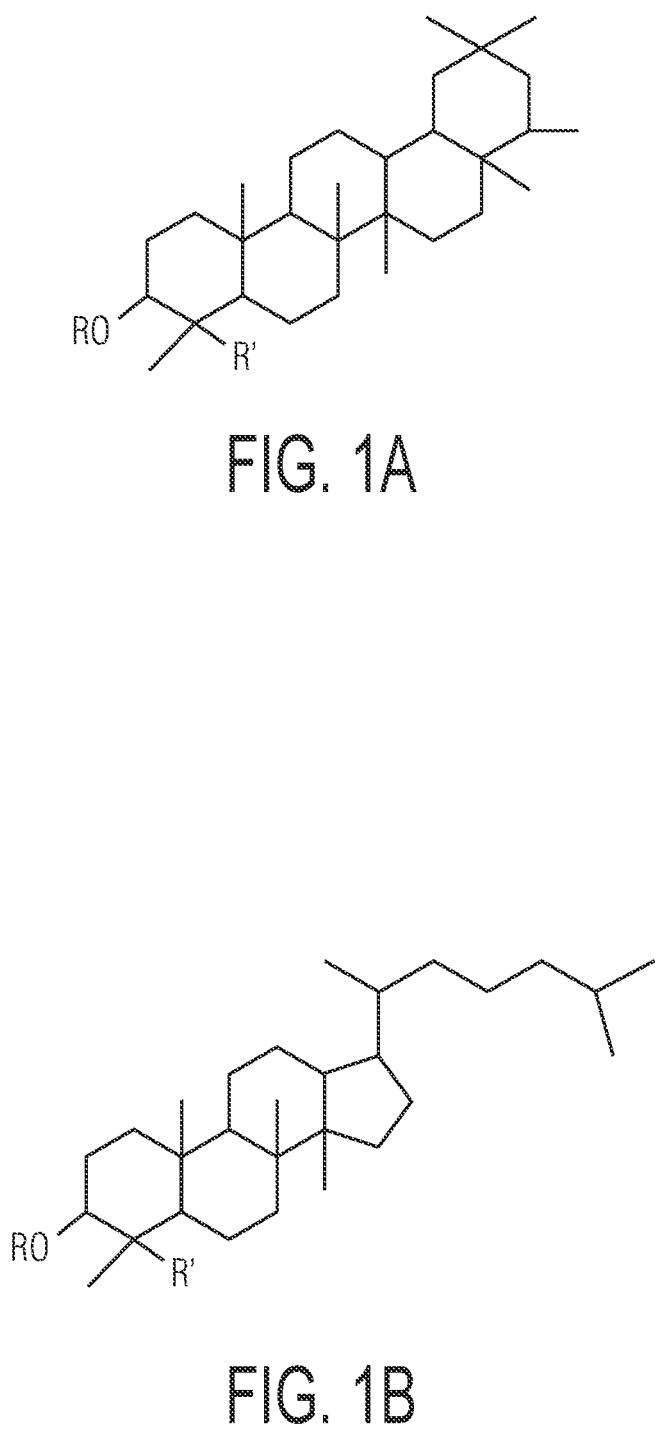

As used herein the term "saponin" generally refers to glycosides comprising a sugar component referred to as a glycone and a non-sugar component referred to as an aglycone. Depending on the structure of the aglycone the saponin may be classified as a triterpenoid saponin, illustrated in FIG. 1A, or to steroidal saponin, illustrated in FIG. 1B. The aglycone portion of the saponin may be either a pentacyclic triterpenoid or a tetracyclic triterpenoid, both of which contain 30 carbon atoms. Whether steroidal or triterpenoid, saponins may be mono, bi- or tridesmodic. Monodesmodic saponins have a single saccharide, normally attached at C-3. Bidesmodic saponins have two saccharides, often with one attached through an ether linkage at C-3 and the other either attached through an ester linkage at C-28 or through an ether linkage at C-20 (pentacyclic and tetracyclic triterpene saponins, respectively), or through an ether linkage at C-26 (furostane saponins). In certain instances, *Hesperaloe* biomass may comprises at least about 5 wt % of total saponins, such as from about 5 to about 15 wt %, such as from about 8 to about 12 wt %, based upon the bone dry weight of the biomass. Total saponins may be determined as described in the Test Methods section below.

As used herein the term "water soluble solids" generally refers to dry matter which remains after the extract has been centrifuged, filtered and all water is evaporated. The procedure for measuring water soluble solids of a biomass extract of the present invention is described in detail in the Test Methods section below. Water soluble solids may be expressed on a percentage basis relative to the mass of bone dry biomass.

As used herein the term "water insoluble solids" generally refer to the fraction of extract that is removed by centrifugation and filtration in the course of measuring water soluble solids, as described in the Test Methods section below.

DETAILED DESCRIPTION

The present invention relates to novel pharmaceutical, dietary supplements and food ingredient compositions comprising at least one component selected from the extract(s), fraction(s), active compound(s) and phytochemical(s) or mixtures thereof derived from non-woody plants of the genus *Hesperaloe* including, for example, *Hesperaloe funifera, Hesperaloe nocturna, Hesperaloe parviflora*, and *Hesperaloe chiangii*, optionally containing one or more of pharmaceutically and dietetically acceptable phytochemical actives, diluents, vehicles, carriers and actives or mixtures thereof. In a particularly preferred embodiment, the present invention provides an animal feed additive comprising water soluble solids derived from non-woody plants of the genus *Hesperaloe*. Preferably the water soluble solids comprise at least about 5 wt % saponin, more preferably at least about 10 wt % saponin and still more preferably at least about 15 wt % saponin, such as from about 5 to about 30 wt % saponin, such as from about 15 to about 25 wt %.

The compositions of the present invention are particularly well suited for the treatment of non-human-animals including, for example, bovine, fowl, porcine, ovine, and equine species. By way of example, the methods and compositions of the invention can be used for the treatment of cattle, chickens, turkeys, ducks, quail, geese, pigs, and sheep. In a particularly preferred embodiment, the methods and compositions of the present invention can be used for the treatment of poultry and more particularly for the prevention and treatment of coccidiosis.

In certain embodiments, the novel immunological compositions, dietary supplements, and food ingredient of the present invention comprise a mixture of saponins, particularly steroidal saponins. In this manner the compositions of the present invention may comprise least 5 wt %, based upon the bone dry weight of the composition, saponins as measured by the total saponin assay set forth in the Test Methods section below. In a particular embodiment, the saponin containing composition used in accordance with the invention comprises at 10 wt % saponin, more preferably at least about 10 wt % saponin and still more preferably at least about 15 wt % saponin, such as from about 5 to about 30 wt % saponin, such as from about 15 to about 25 wt %. It is believed that the effects of the composition are related to the total amount of saponins present. Thus, one of skill in the art will appreciate that if a certain amount of saponins is desired it can be achieved either through varying the volume of a certain concentration composition administered, varying the concentration of a certain volume of a composition, or both.

Saponins useful in the present invention may also be extracted from non-woody plants of the genus *Hesperaloe*. *Hesperaloe* derived saponins generally have steroidal saponins. Saponins derived from *Hesperaloe* may have at least one of the following aglycones or genins: kammogenin, manogenin, gentrogenin, hecogenin, tigogenin, sarsapogenin, chlorogenin and gitogenin or their corresponding isomer or oxidized or reduced forms with at least one of the following glycosidic moieties (in the form of acid or salt): glucose, xylose, rhamnose, arabinose, or galactose. In other embodiments the steroidal saponins may comprise agamenoside, agaveside, agavoside, magueyside, agavasaponi, cantalasaponin, sisalsaponin, gabrittonoside, dongnoside or amolonin, or other steroidal saponins.

Extractives may be recovered from non-woody plants of the genus *Hesperaloe* by extracting biomass, particularly the leaves and more particularly the leaves above the crown of the plant, with at least one solvent selected from the group consisting of water, methanol, ethanol, butanol, and isopropanol, and mixtures thereof. For example, in one embodiment, the process comprises contacting biomass with an extractant solution comprising water and separating the water soluble fraction from the insoluble biomass fraction. In other embodiments the extractant solution may comprise, in addition to water, a surfactant, a solvent and optionally extract-bearing juice. The extract-bearing juice can come from, for example, an earlier extraction step or an earlier milling step.

A simple water extraction of *Hesperaloe* biomass may yield a crude aqueous extract comprising saccharides, polysaccharides, inorganic salts, saponins and sapogenins. A crude extract may also be produced using methanol as a solvent, or a mixture of methanol and water, to extract biomass, which may have been previously extracted with acetone or diethyl ether to remove lipids and pigments. In other instances, the biomass may be extracted with a 4:1 ethanol-water solvent, followed by subsequent defatting of the extract with a non-polar solvent such as hexane. In certain instances, the defatted extract may be subjected to further treatment to isolate specific water soluble components, such as saponins, which may be purified from the defatted extract by mixing with butanol and separating the butanol phase to yield a mixture of saponins that are substantially free from proteins and free saccharides and polysaccharides.

Hot aqueous extractants can also be used. For example, in one embodiment water soluble solids may be extracted from *Hesperaloe* biomass, particularly the leaves, by extracting the biomass with hot aqueous ethanol or isopropanol (75 to 95% by weight alcohol). The aqueous alcohol extraction fluid may then be filtered and concentrated, and the fat-soluble material may be removed by mixing the extraction fluid with a non-polar solvent such as hexane. A substantially pure saponin composition may then be prepared by further extracting defatted extract with a polar solvent such as butanol.

For the purpose of preparing the compositions of the present invention a simple aqueous extract may be preferred, although other extraction methods are within the scope of the present invention. In a particularly preferred embodiment, *Hesperaloe* biomass may be cut to size, pressed, and extracted with an aqueous solvent to remove water soluble extracts such as inorganic salts, saccharides, polysaccharides, organic acids and saponins. The water soluble extracts are collected and may be concentrated by techniques well known in the art such as, for example, evaporation, spray-drying, drum drying and the like. The extract may be concentrated until it has a solids content of about 20 to about 100% solids by weight, such as from about 20 to about 95% solids by weight, such as from about 20 to about 80% solids by weight.

As will be described in more detail below, the biomass may be milled to separate the bagasse and water soluble solids using a roll, screw, and other forms of presses. In certain preferred embodiments biomass is passed between one or more nips of opposed counter-rotating rolls to maximize the mechanical removal of juice. The bagasse can then be contacted with the juice in a subsequent milling step, as will be described more fully below. In certain instances, the biomass may be cut to size and cleaned prior to milling. Cutting and cleaning may be carried out using well known methods in the art. In a particularly preferred embodiment, the biomass is cleaned to remove debris such as dirt without the use of water or other solvents.

In other embodiments the water soluble solids may be recovered from biomass by diffusion. In diffusion, the biomass brought into contact with the liquid to extract the liquid components. Usually, the biomass is prepared by first cutting, but not shearing or crushing so as to minimize the damage to fibers and avoid the creation of an excessive amount of fines. The prepared biomass is then washed repeatedly, usually using a solvent, to extract the liquid contained in the biomass. The solvent can be any of the foregoing solvents. An exemplary treatment solvent is water, particularly hot water such as water heated to a temperature from about 40 to about 90° C. The solvent can be circulated and reused so that the solvent used for a first extraction is reused as a solvent to extract subsequent prepared biomass.

Various types of diffusers are known in the art and can be adapted for use with biomass as described herein. Suitable diffusers include a ring diffuser, a tower diffuser, or a drum diffuser. Exemplary diffusion systems are discussed, for example, in U.S. Pat. Nos. 4,182,632, 4,751,060, 5,885,539 and 6,193,805 the contents of which are hereby incorporated in a manner consistent with the present disclosure. Numerous other diffusion methods and devices for the diffusion method are known and can be adapted for use in the methods described herein. One such diffuser is the continuous-loop, counter-current, shallow-bed Crown Model Ill Percolation Extractor, commercially available from Crown Iron Works, Blaine, MN.

The biomass, cut or uncut, may be extracted by any suitable extraction process as discussed above. In a particularly preferred embodiment, the solvent used for extraction comprises water. One of skill in the art will recognize the ratio of extraction solvent to biomass will vary based on the solvent, the amount of biomass to be extracted and the extraction procedure. In certain preferred embodiments, the extraction solvent is water and the ratio of extraction solvent to biomass, on the basis of liters of extraction solvent to kilogram of bone-dry biomass, is from about 1:5 to about 1:100, such as from about 1:5 to about 1:50 and more preferably from about 1:5 to about 1:20.

The pH of the extraction solvent can be between about pH 5.0 and 8.0, such as, for example, between about pH 6.0 and about pH 8.0, between about pH 6.5 and about pH 7.5. In a particular embodiment, the extraction solvent is water having a pH between about pH 6.5 and about pH 7.5. In those embodiments where extraction includes imbibition with a crude juice, the imbibition fluid may have a pH from about 4.0 to about 5.0.

The extraction may be carried out at temperatures between about 25 and about 90° C., such as, for example, between about 30 and about 80° C., between about 35 and about 75° C., between about 40 and about 70° C., between about 45 and about 65° C. or between about 50 and about 60° C.

In embodiments where the extraction process is a batch extraction process, the duration of extraction may range from about 0.25 to about 24 hours, such as, for example, from about 0.5 to about 2 hours, from about 1 to about 8 hours, or from about 1 to about 6 hours.

In embodiments where the extraction process is a continuous process, the duration of extraction may range from about 0.25 to about 5 hours, such as, for example, from about 0.5 to about 3 hours.

After extraction the water insoluble biomass material may be separated from the water soluble solids by filtration to provide a filtrate containing inorganic salts, saccharides, polysaccharides, organic acids and saponins (referred to herein as the "first filtrate"). Separation can be achieved by any suitable means including, but not limited to, gravity filtration, a plate-and-frame filter press, cross flow filters, screen filters, Nutsche filters, belt filters, ceramic filters, membrane filters, microfilters, nanofilters, ultrafilters or centrifugation. Optionally various filtration aids such as diatomaceous earth, bentonite, zeolite, and the like, may also be used in this process.

After separation, the pH of the first filtrate may be adjusted to remove additional impurities. In one embodiment, the pH of the first filtrate can be adjusted to between about 8.5 and about 10.0 by treatment with a base, such as, for example, calcium oxide or hydroxide (about 1.0% from the volume of filtrate) with slow agitation.

In a particularly preferred embodiment water soluble solids are removed from biomass by a series of mills, such as two, three, four, five, six or seven mills arranged in tandem, optionally with imbibition and/or depithing. Generally, processing biomass according to the present invention removes at least about 25% of the water soluble solids from the biomass, more preferably at least about 50%, still more preferably at least about 75%, such as from about 25 to about 98%, such as from about 50 to about 90%, such as from about 75 to about 90%.

The amount of water soluble solids recovered from biomass may vary depending on the extraction efficiency, however, in certain instances from about 100 to about 400 grams of water soluble solids may be extracted per kilogram of bone dry biomass, such as from about 120 to about 350 grams per kilogram, such as from about 150 to about 300 grams per kilogram. Of the extracted water soluble solids, the total saponins may comprise from about 5 to about 40 wt %, such as from about 10 to about 30 wt %, based upon the bone dry weight of the water soluble solids. In certain instances the amount of total saponins that may be extracted from biomass may range from about 10 to about 400 grams per bone dry kilogram of biomass, such as from about 20 to about 300 grams, such as from about 25 to about 200 grams, such as from about 10 to about 100 grams. In certain instances, the amounts of materials (on bone dry grams per kilogram of bone dry biomass) removed from the biomass during the extraction process may range as set forth in Table 1, below.

TABLE 1

| | Amount (g/kg of bone dry biomass) |
| --- | --- |
| Total Extracted Solids | 100-400 |
| Total Water Insoluble Solids | 5-50 |
| Total Water Soluble Solids | 95-350 |
| Total Saponins | 5-160 |

In addition to saponins, the water soluble solids may comprise saccharides, proteins, lipids, and inorganic salts. For example, in certain instances, the water soluble solids may comprise from at least about 1 wt %, based upon the bone dry weight of water soluble solids, saccharides, such as from about 1 to about 15 wt %, such as from about 2 to about 10 wt %. The saccharides may comprise monosaccharides and oligosaccharides. In other instances, the water soluble solids may comprise from at least about 15 wt %, based upon the bone dry weight of water soluble solids, inorganic salts, such as from about 15 to about 30 wt %.

Generally milling is carried out with the addition of an aqueous solvent, such as water, having a pH ranging from about 5 to about 9, such as from about 6 to about 7 to about 8. The water soluble solids are generally recovered from the milling process as a crude extract and may be subjected to further processing to recover specific compounds, such as saccharides, polysaccharides, organic acids and saponins.

The suspended solids, also referred to herein as the water insoluble fraction, may optionally be removed from the crude extract by well-known processes including, for example, clarification, filtration, centrifugation, or a combination thereof. The amount of water insoluble solids in the extract (on bone dry grams per kilogram of bone dry biomass) may range from about 1.0 to about 30 grams and may comprise hydrophobic substances such as waxes and the like.

After removal of suspended solids, the clarified juice may be used directly, concentrated, or subjected to further processing to isolate one or more water soluble solids such as saccharides, polysaccharides, organic acids, saponins and sapogenins. In other instances, the clarified juice may be further purified to remove saccharides, polysaccharides, and organic acids to yield composition comprising saponins.

The juice resulting from the foregoing extraction process may be subjected to further extraction to obtain saponin in the form of a crude saponin extract or its substantially purified form comprising saponins at a concentration from about 30 to about 90% in weight. The extraction method may comprise mixing juice extracted from non-woody plants of the genus *Hesperaloe* with a water-immiscible polar solvent. Suitable water-immiscible polar solvents include, for example, alcohols having from 4 to 6 carbon atoms, such as butyl, amyl, hexyl and cyclohexyl alcohols. Extraction of the juice with a water-immiscible polar solvent generally removes impurities such as proteins, carbohydrates, and organic acids, which remain in the aqueous phase, the saponin being transferred to the solvent phase.

The solvent phase containing the saponin may be subjected to further treatment to separate the saponin from the alcohol phase. This can be accomplished in various ways including, for example, by cooling, by dehydrating the solvent extract, or by adding an organic solvent which is miscible with the alcohol solvent but in which the saponin is insoluble. Suitable precipitating solvents include, for example, diethyl ether, petroleum ether, acetone, and chloroform.

In a particularly preferred embodiments, the saponin is separated from the alcohol by flash evaporation. Flash evaporation is a technique known in preparative chemistry for the rapid removal of a volatile component from a liquid mixture. The volatile liquid is removed from solution by rapid conversion to a vapor phase by creating a thin film of the solution over a large surface area under reduced pressure often accompanied by an increase of temperature of the solution above ambient but less than the boiling point of the solution at atmospheric pressure. The actual thickness of the film and the area over which it is applied is chosen to provide optimum evaporation and ease of use, but evaporation may be substantially instantaneous (hence the name "flash" evaporation). Flash evaporation avoids the prolonged use of high temperatures that may degrade the intended product and has the ability to remove almost all of the alcohol component (which makes the remaining solution suitable for the preferred practice of spray drying employed in the next step. The alcohol may be recovered from this step and re-used in the extraction process.

The saponin content of the alcohol extract can be further increased by passage over an ultrafiltration membrane without significant alteration to or loss of the saponin composition. This concentrated saponin fraction where the saponin content is in the range of 85-90%, can then be further purified in a liquid state or reduced to a dry state. Individual saponins may be recovered by a combination of reversed-phase solid phase extraction and preparative reversed-phase HPLC. Alternatively, the alcohol extract containing saponins can be fractionated directly by a combination of reversed-phase solid phase extraction and preparative reversed-phase HPLC.

In still other embodiments saponins may be purified from juice prepared according to the present invention comprises the steps of mixing the juice with a salt and a solvent to form a first solution. The solvent may comprise one or more solvents selected from acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme, 1,2-dimethoxyethane, dimethylformamide, dimethylsulfoxide, 1,4-dioxane, ethanol, ethyl acetate, ethylene glycol, glycerin, heptane, hexamethylphosphoramide, hexamethylphosphorous triamide, hexane, methanol, methyl-t-butyl ether, methylene chloride, N-methyl-2-pyrrolidinone, pentane, perchloroethylene, petroleum ether, 1-propanol, 2-propanol, pyridine, tetrahydrofuran, toluene, triethylamine, trifluorotoluene, water, xylene, or any combination of the forgoing. In some embodiments the solvent is water. The salt may be selected from an alkali metal salt, an alkaline earth salt, a transition metal salt, an ammonium salt, or combinations of the forgoing. In certain preferred embodiment the salt added to the plant extract to form the solution is an alkaline earth metal salt. In particularly preferred embodiments the salt is calcium chloride ($CaCl_2$), magnesium chloride ($MgCl_2$), or a mixture thereof.

The pH of the first solution is generally adjusted to a pH from about 6.0 to about 9.0, such as from about 6.0 to about 8.0, such as from about 6.0 to about 7.0. At least one phosphate may then be added to the first solution to form an ion-polysaccharides complex precipitate. Useful phosphates include, for example, sodium hydrogen phosphate (Na$_2$HPO$_4$), sodium dihydrogen phosphate (NaH$_2$PO$_4$), sodium phosphate (Na$_3$PO$_4$), or sodium hydrogen bisphosphate (Na$_2$H$_2$PO$_7$).

The precipitated ion-polysaccharides complex may be removed by filtration to yield a second solution, which may be further clarified to produce an extract of purified saponins. Optionally, the extract can be concentrated by any filtration technique known in the prior art. Preferably, the concentration of the extract of purified saponins is carried out by nanofiltration, ultrafiltration and diafiltration, or any combination of these techniques. In some embodiments, the saponin extract is substantially free of proteins. In some embodiments, the saponin extract is substantially free of polysaccharides. In some embodiments, the saponin extract is substantially free of phenolic compounds.

In still other embodiments saponins may be extracted from *Hesperaloe* biomass by milling the biomass at extracting at room temperature with a solution of 90% acetonitrile in water with sonication followed by filtration and removal of the solvent under vacuum. Saponins may be further purified by high performance liquid chromatography using CHCl$_3$-MeOH-water (4:4:2 v/v) to yield various fractions that may be recrystallized from MeOH.

The total amount of saponins that may be extracted from *Hesperaloe* biomass according to the present invention may range from about 10 to about 100 grams per bone dry kilogram of biomass, such as from about 20 to about 80 grams, such as from about 25 to about 75 grams. The saponins may be provided as part of a crude juice, as part of a dried water soluble solids compositions, as a partially purified compositions or as a substantially pure composition comprising a mixture of saponins.

Figure 2B:
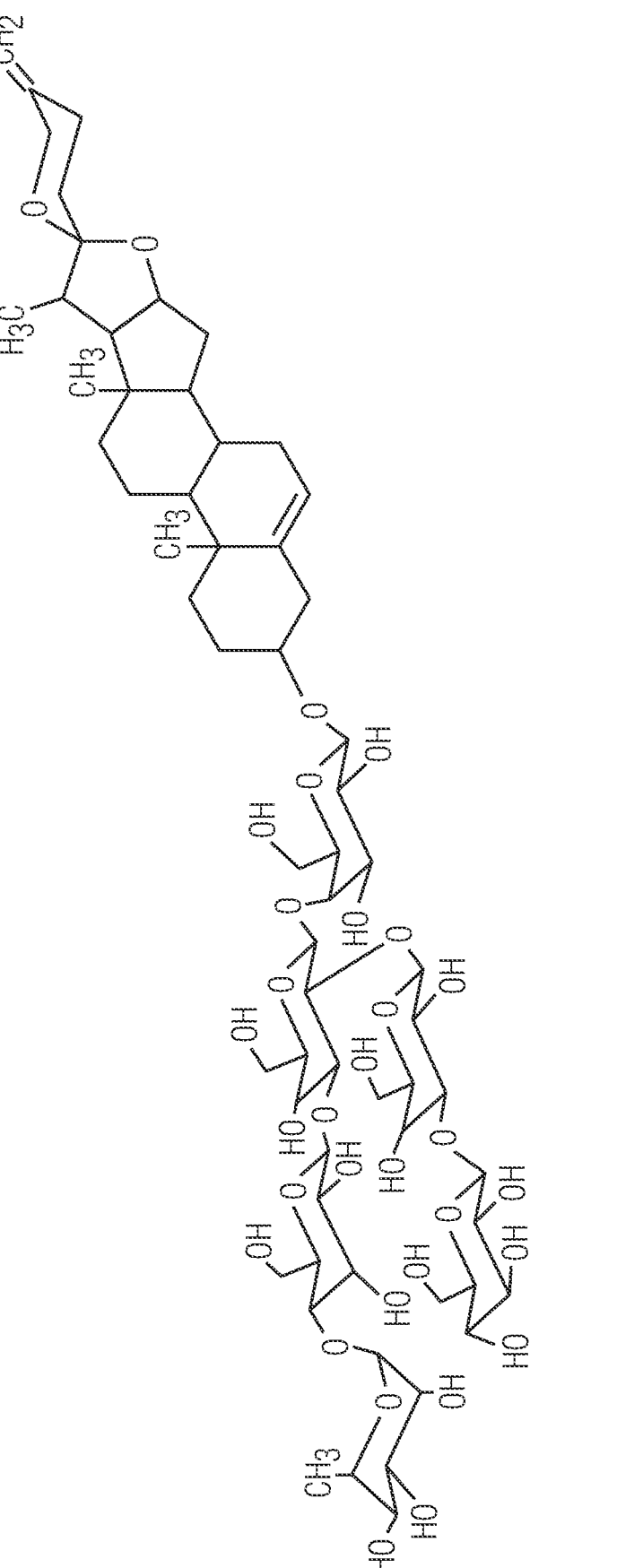
Figure 2C:
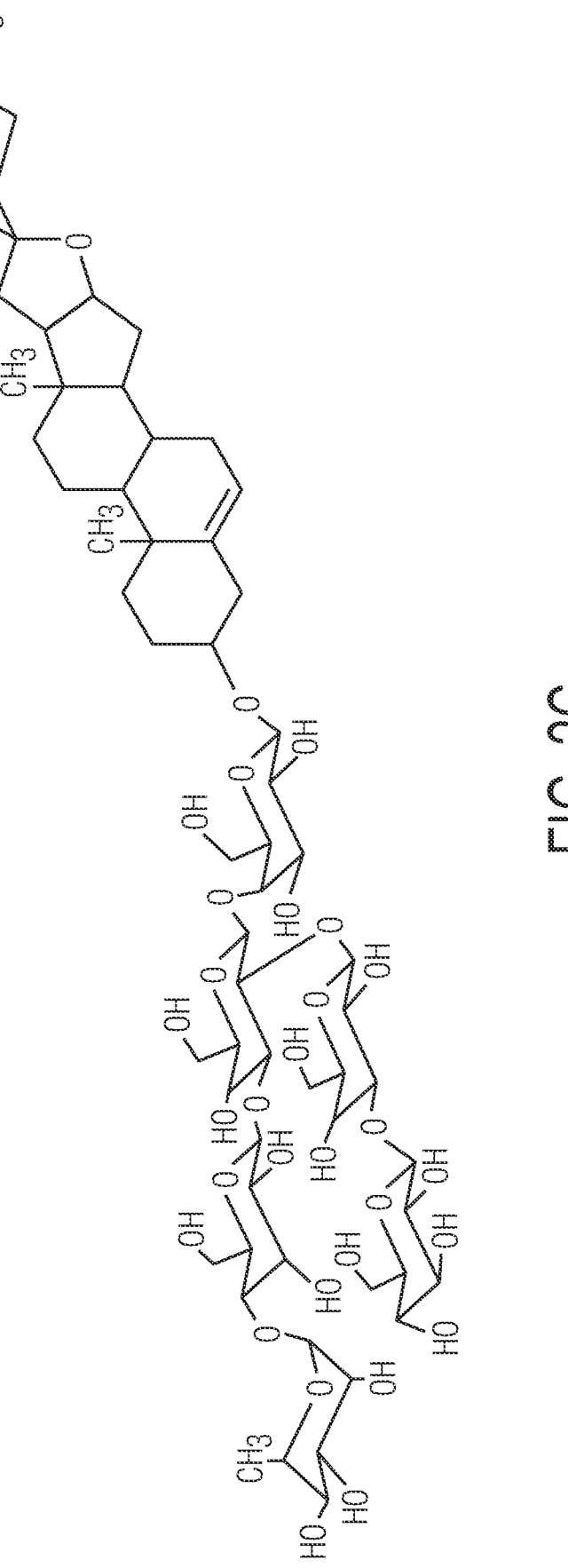

In certain embodiments saponins extracted from *Hesperaloe* biomass may comprise 25(27)-dehydrofucreastatin (FIG. 2A), 5(6),25(27)-disdehydroyuccaloiside (FIG. 2B), 5(6)-disdehydroyuccaloiside (FIG. 2C), furcreastatin and yuccaloiside.

Compositions useful in the present invention may be prepared by blending an aqueous extract from *Hesperaloe* biomass with one or more polyhydroxy alcohols including glycerol, propylene glycol, polyalkylene glycol such as polyethylene glycol and polypropylene glycol, and polyglycerol. Preferred polyhydroxy alcohols have less than about eight carbon atoms. Glycerol and propylene glycol are particularly preferred polyhydroxy alcohols.

The composition may also comprise saccharides, which may be present in the aqueous extract or may be added after extraction during formulation. Saccharides useful in compositions of the present invention include monosaccharides such as glucose, disaccharides such as sucrose and polysaccharides such as starch.

In still other embodiments compositions in accordance with embodiments of the invention can include various other additives known in the art to have benefits for the maintenance and well-being of non-human animals. By way of example, compositions can also include components such as Vitamin E, Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey.

Saponin containing compositions of the present invention may be in liquid or dry forms. By way of example, a saponin containing *Hesperaloe* extract may be dried into a powder form. In this form, the saponin containing composition may be administered to an animal as a pill or bolus or mixed in with other components such as a feed ration. For example, dry powder formulations of saponin containing compositions may be added to the feed ration via a micro-ingredient machine or added to a feed mix truck and mixed thoroughly to assure even distribution in the feed. Saponin containing extracts may also be formulated as liquid with water as the carrier and be administered to an animal as a liquid drench.

Saponin containing compositions of the present invention may be administered to non-human animals in need there of as a single dose, as multiple doses as part of a feeding regiment. For example, a non-human animal may receive an initial dose and then receive subsequent maintenance doses in lesser amounts. A non-human animal may receive multiple doses of a saponin containing composition in one day or may receive multiple doses over multiple days.

In certain embodiments, non-human animals, especially birds and more particularly poultry, can be treated with a saponin containing composition in an amount that is effective to improve the feeding characteristics of an animal and/or improve the production characteristics of an animal in comparison to an untreated control animal. Production characteristics can include carcass quality grades, yield grades, average daily gain, and the like. In an embodiment, when administered as a feed additive to poultry, the amount of saponins per 100 kilograms of feed is preferably at least about 1 g/100 kg, such as from about 1 to about 50 g/100 kg, such as from about 2 to about 40 g/100 kg.

The basal animal feed may be a dry feed, or a liquid feed and the compositions of the present invention may be formulated as a liquid, a slurry, a dry powder, a dry granular mix, a paste, a pellet, or a block. Suitable feeds may be prepared by applying saponins containing extracts, such as my mixing or spraying, with suitable basal animal feeds commonly employed in the feeding of animals. Typical basal animal feeds useful in the present invention may comprise one or more of corn meal, corncob grits, soybean meal, alfalfa meal, rice hulls, soybean mill run, cottonseed oil meal, bone meal, ground corn, corncob meal, wheat middlings, limestone, dicalcium phosphate, sodium chloride, urea, distillers dried grain, vitamin and/or mineral mixes, cane molasses or other liquid carriers and the like. Such basal animal feeds promote a uniform distribution and administration of the saponins.

In still other embodiments, the compositions of the present invention, may be useful as an immunostimulatory, immunopotentiator or adjuvant. For example, in certain preferred embodiments compositions of the present invention may be administered with an *Eimeria* vaccine to poultry in need thereof to increase the immune response, lower lesion scores and reduced oocyst shedding resulting from coccidiosis. The immunogenic composition of the present invention may be delivered orally or subcutaneously in a dose volume suitable for increasing an immune response, such as a does level of less than about 50 µg, such as less than about 40 µg, such as less than about 30 µg, such as from about 1 to about 50 µg, such as from about 5 to about 30 µg.

In one embodiment the present invention provides a vaccine composition comprising an antigen and a saponin extracted from a non-woody plant of the genus *Hesperaloe*. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

In a particularly preferred embodiment, the present invention provides a method of enhancing the immune response of the non-human animal comprising administering to a non-human animal in need thereof a saponin extracted from a non-woody plant of the genus *Hesperaloe* and an antigen.

In certain preferred embodiments the compositions of the present invention may be administered with a vaccine intended for the prevention of coccidiosis in non-human animals, in particular poultry, characterized in that the coccidia are chosen from the group consisting of *Eimeria, Isospora, Toxoplasma, Besnoitia,* and *Neospora.* Thus, the present invention provides an adjuvant system that is particularly advantageous in making and using vaccine and other immunostimulant compositions to treat or prevent diseases, such inducing active immunity towards antigens in non-human animals.

The compositions of the present invention exhibit adjuvant effects when administered over a wide range of dosages and a wide range of ratios to the antigen being administered. In one embodiment, the weight ratio of total saponins to antigen is 3.0 or less, preferably 1.0 or less.

Saponins may be used as adjuvants in crude or purified forms and may be admixed with other non-saponin adjuvants to achieve the enhancement of the Immune response to an antigen. Such non-saponin adjuvants useful with the present invention are oil adjuvants (for example, Freund's Complete and Incomplete), liposomes, mineral salts (for example, $AlK(SO_4)_2$, $AlNa(SO_4)_2$, $AlNH$, $(SO_4)$, silica, alum, $Al(OH)_3$, Ga, $(PO_4)_2$, kaolin, and carbon), polynucleotides (for example, poly IC and poly AU acids), and certain natural substances (for example, wax D from *Mycobacterium tuberculosis,* as well as substances found in *Corynebacterium parvum, Bordetella pertussis*, and members of the genus *Brucella*).

Test Methods

Water Soluble Solids

Total biomass water soluble solids may be determined using an Accelerated Solvent Extraction system (ASE) such as a Dionex™ ASE™ 350 (Thermo Fisher Scientific, Waltham, MA). Approximately 10 grams of harvested biomass is dried to a constant weight in an oven, typically 4 hours at 125° C. After drying 1.5-2.0 grams of the bone dry biomass is accurately weighed and the weight ($W_b$) recorded to the nearest 0.001 gram. Using water as the solvent, biomass is extracted using the conditions set forth in the table below. The ratio of biomass to solvent is generally 21:1 and five consecutive water extraction cycles are performed. At the end of each extraction cycle, the liquid phase is collected, dried under vacuum at approximately 40° C. and the weight of the dried material ($W_1$) is recorded to the nearest 0.001 g. The total weight of water soluble solids ($W_e$) is calculated by summing the weight of solids recovered from each extraction cycle ($W_1$). Total water soluble solids as a percentage of bone dry biomass is then determined using the following equation: Water Soluble Solids (wt %)=$W_e/W_b*100$.

| | |
|---|---|
| Pressure (psi) | 1500 |
| Temperature (° C.) | 40 |
| Static Time (min.) | 10 |
| Cycles (no.) | 5 |

The total water soluble solids in biomass extract may be determined by withdrawing an appropriate aliquot, typically about 10-50 ml, transferring to clean, dry, centrifuge tube. The tube is centrifuged at 7000 rpm for 20 minutes. The weight of extract ($W_1$) is calculated. An aliquot of the supernatant is then transferred to clean, pre-weighed beaker ($D_0$), and weighed. The beaker and sample are then weighed to the nearest 0.001 g and the weight ($D_2$) recorded. The beaker containing the sample is then placed at 140° C. in a hot air oven for overnight drying. The beaker is removed from the oven and desiccated to cool to room temperature then weighed to the nearest 0.001 gram ($D_1$). The weight percentage of soluble solids, based upon the weight of the extract, is determined using the formula below:

$$\text{Water Soluble Solids}\,(wt\ \%) = \frac{(D_1 - D_0)\times 100}{(D_2 - D_0)}$$

$D_1$=mass of empty beaker+dried soluble solids, $D_0$=mass of empty beaker, $D_2$=mass of biomass extract and empty beaker.

Total Saponins

Total saponins were measured generally as described in Makkar, Harinder P. S., Sidhuraju, P., Becker, Klaus (2007) Plant Secondary Metabolites, chapter 17, pp 93-100. A standard saponin solution was prepared by weighing 10 mg of diosgenin (MilliporeSigma>93%), dissolving in 16 mL of methanol and adding 4 mL of distilled water. The solution was mixed thoroughly to yield a 0.5 mg/mL diosgenin solution in 80% methanol solvent. The standard was used to produce a calibration curve by transferring various amounts of the standard (0, 10, 20, 40, 60, 80, and 100 μL) into 13-mm glass test tubes. A solution of 80% aqueous methanol was added to a total volume of 100 μL.

Prior to testing samples of biomass extract were adjusted to about 0.5 wt % total solids by dilution with water to ensure absorbency result fell along the saponin standard calibration curve range. Samples of diluted extract (20-μL) were pipetted into 13-mm glass test tubes and the volume was brought up to 100 μL with 80 μL methanol. Each sample was tested in triplicate.

To each sample 100 μL of vanillin reagent (prepared by dissolving 800 mg of vanillin in 10 mL of 99.5% ethanol (analytical grade)) and then 1.0 mL of 72% (v/v) sulfuric acid (72% (v/v) sulfuric acid prepared by adding 72 mL of sulfuric acid (analytical grade, 95%, w/w) to 28 mL of distilled water) were added. Solutions were mixed well and heated at 60° C. for 10 minutes. Samples were then cooled in an ice bath and 1 mL of solution was transferred into respective cuvette and absorbance at 544 nm was read. The total mass of saponins in the sample may be calculated based upon the standard absorbency curve as follows:

Saponin (μg)=[Slope]×Measured Absorbency−[Intercept]

EXAMPLES

Example 1

A total of 150 one-day-old broiler chicks were randomly distributed to six experimental groups in a 28-day cage study. Live coccidia were manually introduced to the birds at their 14th day of age. The treatment codes, listed in Table 2, included two control codes using basal diet with (Control+) and without (Control) coccidian challenges. Remaining treatment codes were all challenged with coccidian using base diet enriched with an inventive composition at two different dosages or a *Yucca* extract marketed under the tradename FOAMATION™ (commercially available from Ingredion, Westchester, IL). FOAMATION™ comprised 50% by weight of the composition water soluble solids, of which saponins comprised 10 wt %. Bird body weight gain (BW) and feed consumption for each pen were measured on a weekly basis. Feed conversion rate (FCR) is the ratio between kilograms of feed consumed and kilograms of body weight gain. The lower FCR value indicates a better feed.

TABLE 2

| Codes | Feed Add-on (g/100 kg of feed) | Saponin Add-on (g/100 kg of feed) |
|---|---|---|
| Control | 0 | — |
| Control+ | 0 | — |
| Inventive (low dose) | 520 | 1 |
| Inventive (High dose) | 800 | 41 |
| FOAMATION ™ | 20 | 1.0 |

The inventive extract was prepared by forage harvesting mature *Hesperaloe funifera* leaves above the crown, cutting the leaves into pieces ranging from about 0.50 to about 8.0 cm and pressing the cut biomass using a tandem press. The biomass was pressed three times and the crude juice was collected and passed through 25 mm filter and heated to concentrate the extract to 29% solid. The water soluble solids comprised 21 wt % total saponins, based upon the bone dry weight of water soluble solids.

At the end of 28-day trial, the challenged control (Control+) group decreased feed consumption by about 140 g/bird and body weight gain by was reduced by about 160 g/bird compared to the control without challenge. These decreases, however, were not observed in chickens administered feeds comprising the inventive composition, as illustrated in Table 3, below.

TABLE 3

| Code | Feed Consumption (kg/bird) | Body Weight Gain (kg/bird) | Feed Conversion Rate |
|---|---|---|---|
| Control | 2.09 | 1.25 | 1.67 |
| Control+ | 1.95 | 1.09 | 1.78 |
| Inventive (low dose) | 2.03 | 1.21 | 1.68 |
| Inventive (High dose) | 2.09 | 1.22 | 1.71 |
| FOAMATION ™ | 2.02 | 1.21 | 1.67 |

Example 2

A total of 512 one-day-old broiler chicks were randomly distributed to 8 experimental groups, 8 cages for each group and 8 birds per cage in a 21-day study. Live coccidian was manually introduced to the young birds at 14th day of age. Bird weight gain (WG), feed conversion rate (FCR), lesion score and oocyst counts were measured. The treatment codes, listed in Table 4, included basal diet with no coccidian challenge (control) and with challenge (Control+). Remaining treatment codes were coccidian challenged codes using base diet with Coban (commercially available from Elanco Animal Health, Greenfield, IN), Micro-Aid Green (commercially available from DPI Global, Porterville, CA) and two different inventive samples at two different dosages. Base diet met the minimum National Research Council requirements for poultry.

TABLE 4

| Code | Code Details | Active Loading (g/100 kg base feed) |
|---|---|---|
| Control | No challenge; No medication | 0 |
| Control + Cocci | Challenge; No medication | 0 |
| Coban | Challenge; Anti-coccidiosis Drug | 9 |
| Invention | Challenged; Low dose Sample 1 | 1.6 |
| Invention | Challenged; High dose Sample 1 | 29.9 |
| Invention | Challenged; Low dose Sample 2 | 1.6 |
| Invention | Challenged; High dose Sample 2 | 29.9 |
| Micro-Aid | Challenged; Micro-Aid | 1.6 |

Inventive sample 1 was prepared by forage harvesting mature *Hesperaloe funifera* leaves above the crown, cutting the leaves into pieces ranging from about 0.50 to about 8.0 cm and pressing the cut biomass using a tandem press. The biomass was pressed three times and the crude juice was collected and passed through 25 mm filter and heated to concentrate the extract to 29% solid. Inventive sample 2 was prepared by forage harvesting mature *Hesperaloe funifera* leaves above the crown, cutting the leaves into pieces ranging from about 0.50 to about 8.0 cm and pressing the cut biomass using a tandem press once, followed by heating of the collected juice to obtain an extract having 14% solids. All treatment materials were made by mixing each additive to the base feed at the designated loading level in a mixer.

Chickens fed the inventive composition exhibited weight gain, improved feed conversion rate, decreased lesion score and lower oocysts as summarized in Table 5, below. In many instances the improvements were the comparable to, or better, then those observed in chickens fed Coban or Micro-Aid Green. Even at relatively low dosages of saponin, the inventive compositions were effective.

TABLE 5

| | Performance Over 21 Dyas | | | | Improvement Over Cocci Control | | | |
|---|---|---|---|---|---|---|---|---|
| Code | Weight Gain (kg) | Feed Conversion Rate | Lesion Score | Oocyst (No./g) | Weight Gain | Feed Conversion Rate | Lesion Score | Oocyst |
| Control | 0.538 | 1.523 | 0.0 | 0 | — | — | — | — |
| Control + Cocci | 0.419 | 1.868 | 2.6 | 42830 | — | — | — | — |
| Coban | 0.460 | 1.640 | 1.7 | 15708 | 10% | 4% | 36% | 63% |
| Invention | 0.448 | 1.832 | 2.0 | 38628 | 7% | 3% | 23% | 10% |
| Invention | 0.473 | 1.673 | 2.1 | 29665 | 13% | 5% | 19% | 31% |
| Invention | 0.449 | 1.746 | 1.9 | 28197 | 7% | 3% | 27% | 34% |
| Invention | 0.433 | 1.745 | 1.8 | 17492 | 3% | 1% | 31% | 59% |
| Micro-Aid | 0.452 | 1.752 | 2.0 | 35143 | 8% | 3% | 23% | 18% |

Compositions of the present invention are particularly useful in reducing or preventing coccidial. Lesion score is a means of assessing coccidial development through chicken's intestinal damage on a score between 0-4 (0 indicates normal intestinal appearance while 4 indicates severe damaged intestine). Chickens fed the inventive composition, over 3 weeks, improved lesion score (23-27%), compare to the unchallenged control. By reducing the instances of infection and protecting the chickens' digestive system, the chickens were able to better digest and absorb nutrients and grow at a greater rate.

EMBODIMENTS

First Embodiment: An animal feed composition comprising a basal animal feed; and water soluble solids extracted from a non-woody plant of the genus *Hesperaloe* and comprising at least one saponin.

Second Embodiment: The animal feed composition of the first embodiment wherein the composition is a liquid, a slurry, a dry powder, a dry granular mix, a paste, or a solid.

Third Embodiment: The animal feed composition of the first or the second embodiment wherein the basal animal feed comprises one or more of corn meal, corncob grits, soybean meal, alfalfa meal, rice hulls, soybean mill run, cottonseed oil meal, bone meal, ground corn, corncob meal, wheat middlings, limestone, dicalcium phosphate, sodium chloride, urea or distillers dried grain.

Fourth Embodiment: The animal feed composition of any one of the first through third embodiments wherein the basal animal feed comprises water and is a liquid.

Fifth Embodiment: The animal feed composition of any one of the first through fourth embodiments wherein the total amount of saponin ranges from about 1 to about 100 g per 100 kg of animal feed.

Sixth Embodiment: The animal feed composition of any one of the first through fifth embodiments wherein the at least one saponin consists of kammogenin, manogenin, gentrogenin, hecogenin, tigogenin, sarsapogenin, chlorogenin and gitogenin or their corresponding isomer or oxidized or reduced forms and at least one glycosidic moiety selected from glucose, xylose, rhamnose, arabinose, or galactose.

Seventh Embodiment: The animal feed composition of any one of the first through sixth embodiments wherein the at least one saponin is 25(27)-dehydrofucreastatin (FIG. 2A) 5(6),25(27)-disdehydroyuccaloiside C (FIG. 2B), 5(6)-disdehydroyuccaloiside C (FIG. 2C), furcreastatin or yuccaloiside C.

Eighth Embodiment: The animal feed composition of any one of the first through seventh embodiments wherein the mass of the water soluble solids ranges from about 100 to about 1,000 g per kilogram of basal animal feed.

Ninth Embodiment: The animal feed composition of any one of the first through eighth embodiments wherein the water soluble solids comprise from about 10 to about 25 wt % saponin.

Tenth Embodiment: Administering to a non-human animal the animal feed composition of any one of embodiments one through nine to reduce environmental ammonia and odor, to provide a hypocholesterolemic effect, reduce inflammation, provide an anti-protozoal effect, control parasitic nematodes, promote weight gain or improve feed conversion efficiency.

Eleventh Embodiment: Administered orally to poultry for the prevention and treatment of coccidiosis the animal feed composition of any one of embodiments one through nine.

What is claimed is:

1. An immunological composition useful for inducing the production of antibodies to an antigen in a non-human animal comprising:
   a. an immunogenically effective amount of an antigen; and
   b. an extract comprising water soluble solids comprising at least one saponin, wherein the extract is extracted from a biomass derived from a non-woody plant of the genus *Hesperaloe*, and wherein the water soluble solids comprise at least 5 wt. % saponin, wherein the at least one saponin is 25(27)-dehydrofucreastatin, 5(6),25(27)-disdehydroyuccaloiside C, 5(6)-disdehydroyuccaloiside C, furcreastatin or yuccaloiside C.

2. The immunological composition of claim 1 wherein the composition is a liquid, a slurry, a dry powder, a dry granular mix, a paste, or a solid.

3. The immunological composition of claim 1 wherein the immunological composition comprises from about 1 to about 50 μg of total saponins.

4. The immunological composition of claim 1 wherein the antigen is a microbial pathogen, bacteria, virus, protein, glycoprotein lipoprotein, peptide, glycopeptide, lipopeptide, toxoids, carbohydrate, or tumor-specific antigens.

5. The immunological composition of claim 1 wherein the antigen is a coccidia.

6. The immunological composition of claim 5 wherein the coccidia is chosen from the group consisting of *Eimeria, Isospora, Toxoplasma, Besnoitia* and *Neospora.*

7. The immunological composition of claim 3 wherein the weight ratio of total saponins to antigen is 3.0 or less.

8. The immunological composition of claim 1 wherein the non-woody plant is *Hesperaloe funifera, Hesperaloe nocturna, Hesperaloe parviflora, Hesperaloe chiangii*, or mixtures thereof.

9. An immunological composition useful for inducing the production of antibodies to an antigen in a non-human animal comprising:
   a. an immunogenically effective amount of an antigen; and
   b. an extract obtained from a biomass derived from a non-woody plant of the genus *Hesperaloe*, wherein the non-woody plant comprises *Hesperaloe funifera*, wherein the extract comprises from about 10 to about 25 wt % saponin, based upon the bone dry weight of the extract water soluble solids, and wherein the extract comprises a mixture of 25(27)-dehydrofucreastatin, 5(6),25(27)-disde hydroyuccaloiside C, 5(6)-disdehydroyuccaloiside C, furcreastatin and yuccaloiside C.

10. The immunological composition of claim 9 wherein the extract further comprises saccharides, proteins, and lipids.

11. The immunological composition of claim 9 wherein the extract is substantially free from saccharides, proteins, and lipids.

12. The immunological composition of claim 9 wherein the extract comprises at least about 90 wt % water soluble solids, based upon the bone dry weight of the extract.

13. The immunological composition of claim 9 wherein the extract comprises at least about 2 wt % water insoluble solids, based upon the bone dry weight of the extract.

14. A method of treating coccidiosis in poultry comprising administering thereto an anticoccidial amount of a feed composition comprising a basal animal feed; and an extract obtained from a biomass derived from a non-woody plant of the genus *Hesperaloe*, wherein the non-woody plant comprises *Hesperaloe funifera*, wherein the extract comprises from about 10 to about 25 wt % saponin, based upon the bone dry weight of the extract water soluble solids, and wherein the extract comprises a mixture of 25(27)-dehydrofucreastatin, 5(6),25(27)-disdehydroyuccaloiside C, 5(6)-disdehydroyuccaloiside C, furcreastatin and yuccaloiside C.

15. The method of claim 14 wherein the saponin is provided as a mixture of water soluble solids and the mass of the water soluble solids ranges from about 100 to about 1,000 g per kilogram of animal feed.

16. The method of claim 15 wherein the water soluble solids further comprise saccharides, proteins, and lipids.

17. The method of claim 15 wherein the water soluble solids are substantially free from saccharides, proteins, and lipids.

18. A method of treating coccidiosis in poultry comprising administering thereto an immunogenically effective amount of an antigen and an extract obtained from a biomass derived from a non-woody plant of the genus *Hesperaloe*, wherein the non-woody plant comprises *Hesperaloe funifera*, wherein the extract comprises from about 10 to about 25 wt % saponin, based upon the bone dry weight of the extract water soluble solids, and wherein the extract comprises a mixture of 25(27)-dehydrofucreastatin, 5(6),25(27)-disdehydroyuccaloiside C, 5(6)-disdehydroyuccaloiside C, furcreastatin and yuccaloiside C.

19. The method of claim 18 wherein the extract comprises from about 1 to about 50 µg of total saponins.

20. The method of claim 18 wherein the antigen is a coccidia.

21. The method of claim 20 wherein the coccidia is chosen from the group consisting of *Eimeria, Isospora, Toxoplasma, Besnoitia* and *Neospora*.

\* \* \* \* \*